(12) United States Patent
Granchukoff

(10) Patent No.: US 6,265,792 B1
(45) Date of Patent: Jul. 24, 2001

(54) MEDICAL DEVICE HAVING PRECISION INTERCONNECT

(75) Inventor: Peter I. Granchukoff, El Dorado Hills, CA (US)

(73) Assignee: EndoSonics Corporation, Rancho Cordova, CA (US)

( * ) Notice: Subject to any disclaimer, the term of this patent is extended or adjusted under 35 U.S.C. 154(b) by 0 days.

(21) Appl. No.: 09/392,372

(22) Filed: Sep. 8, 1999

(51) Int. Cl.[7] .................................................. H01H 35/00
(52) U.S. Cl. .............................. 307/116; 73/708; 600/486
(58) Field of Search ................................... 307/112, 116, 307/125; 600/585, 481, 485, 486, 488, 509; 73/708, 756; 439/909

(56) References Cited

U.S. PATENT DOCUMENTS

| | | |
|---|---|---|
| 4,366,714 | 1/1983 | Adorni . |
| 5,163,445 | 11/1992 | Christian et al. . |
| 5,178,159 | 1/1993 | Christian . |
| 5,240,437 | 8/1993 | Christian . |
| 5,348,481 | 9/1994 | Ortiz . |
| 5,375,596 | * 12/1994 | Twiss et al. ........................... 128/903 |
| 5,384,540 | * 1/1995 | Dessel .................................. 324/539 |
| 5,520,644 | * 5/1996 | Imran ..................................... 604/95 |
| 5,666,958 | * 9/1997 | Rothenberg et al. ................. 439/909 |
| 5,715,827 | 2/1998 | Corl et al. . |
| 5,792,194 | * 8/1998 | Morra ..................................... 607/17 |
| 5,903,971 | * 5/1999 | Ishiwata et al. ........................ 29/748 |
| 5,935,079 | * 8/1999 | Swanson et al. ..................... 600/509 |

OTHER PUBLICATIONS

Frank M.L. Van Der Goes and Gerard C.M. Meijer, "A Universal Transducer Interface for Capacitive and Resistive Sensor Elements".

* cited by examiner

Primary Examiner—Josie Ballato
Assistant Examiner—Rios Roberto
(74) Attorney, Agent, or Firm—Leydig, Voit & Mayer, Ltd.

(57) ABSTRACT

An electrical device such as a pressure guide wire (700) which has a resistive pressure sensor, such as a piezoresistive sensor (208), uses a precision interconnect in order to provide proper pressure measurement readings. The precision interconnect helps avoid the effects of contact and line resistance on the measurement of the pressure sensor's resistors (402 and 404). The precision interconnect uses high input impedance device's such as differential operational amplifiers (902, 904) in order to overcome the effect of any changes in the contact resistance. Further, an interface switch (1110) which is responsive to a control signal (1106) automatically determines what type of pressure guide wire (10 or 700) is attached to the interface circuit (1200).

22 Claims, 9 Drawing Sheets

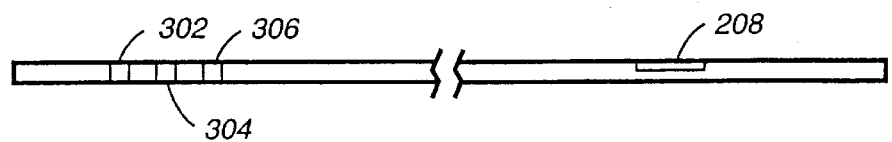
PRIOR ART
FIG. 3   *10*
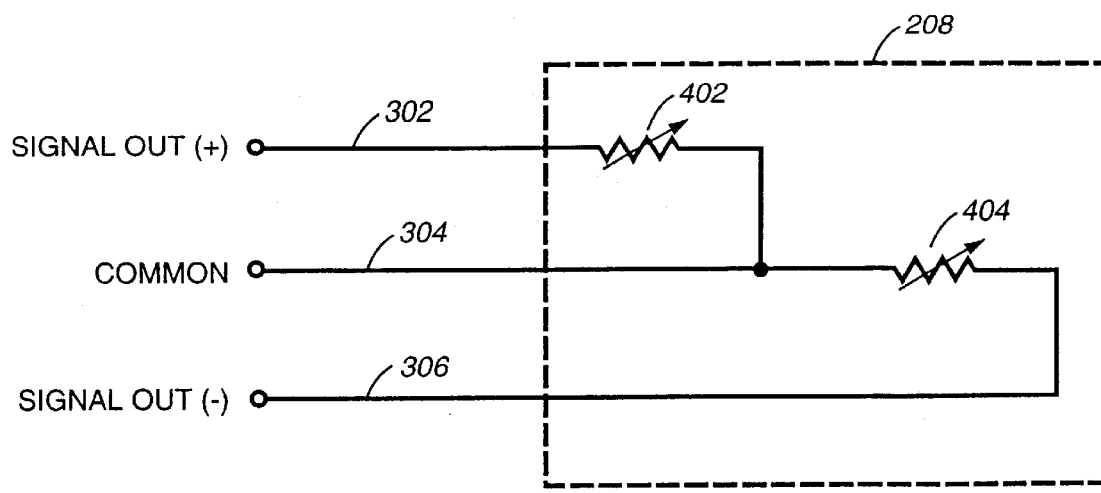
PRIOR ART
FIG. 4

MEDICAL DEVICE HAVING PRECISION INTERCONNECT

TECHNICAL FIELD

This invention relates in general to electrical devices, and more particularly, to an electrical device such as an intravascular pressure guide wire having a precision interconnect.

BACKGROUND

Medical guide wires having miniature pressure sensors are well known. Such pressure guide wires typically have a pressure sensor located at the guide wire's distal end that is used to measure the pressure within a patient's artery. Electrical conductors which are connected to the pressure sensor are passed through the inside of the guide wire to a set of electrical contacts or sleeves located at the proximal end of the guide wire. The electrical contacts on the guide wire are mated to external monitoring equipment using an interface cable. The external monitoring equipment can provide pressure information to the attending physician that is useful in the diagnosis for example of an arterial occlusion. An example of such a pressure guide wire is described in U.S. Pat. No. 5,715,827, entitled "Ultra Miniature Sensor and Guide Wire Using The Same and Method".

In FIG. 1 there is shown a prior art pressure measuring system 100 comprising a guide wire 10 placed within a patient 12. The guide wire 10 is used with apparatus 20 that comprises rotary connector assembly 220 and a cable 214 that connects the rotary connector assembly 220 to an interface box 24. Connector 32 which is part of the rotary connector assembly 220 electrically interconnects with interface box connector 34.

Interface box 24 is connected by cable 26 to a pressure monitoring console 28, such as a WAVEMAP™ pressure monitoring instrument manufactured by EndoSonics, Inc., Rancho Cordova, Calif. Console 28 can display both proximal and distal pressure measurements as will has controls for calibrating the pressure wire 10 prior to its usage.

Referring now to FIG. 2, there is shown a more detailed view of the prior art pressure guide wire 10 coupled to a rotary connector assembly 220. As shown therein, pressure guide wire 10 can be manufactured utilizing the various constructions as shown and described in U.S. Pat. Nos. 5,163,445, 5,178,159 and 5,240,437. Guide wire 10 comprises a flexible elongate element 202 having a proximal and distal extremities 204 and 206 and which can be formed of suitable material such as stainless steel. The guide wire having an outside diameter for example of 0.018 inch or less and having a suitable wall thickness as for example, 0.001" to 0.002" and conventionally called a "hypotube" having a typical length of approximately 150–170 centimeters. A semiconductor pressure sensor 208 is located at the distal extremity of guide wire 10.

The proximal end of guide wire 10 is slid into a rotary connector 210 of the type described in U.S. Pat. Nos. 5,178,159 and 5,348,481 which is part of the rotary connector assembly 220. A torquer 230 is typically clipped-on by a physician distal to the rotary connector 210. Rotation of the torquer 230 causes rotation of guide wire 10 when used in connection with a catherization procedure in a manner well known to those skilled in the art. The proximal extremity 204 of the guide wire 10 is removably disposed within housing 212 of the type described in U.S. Pat. Nos. 5,178,159, 5,348,481 and 5,358,409. Located close to the distal extremity of guide wire 10 is a pressure sensor 208 which is used to measure pressure within a patient's blood vessels.

Electrical contacts located within housing 212 make electrical contact with electrically conductive sleeves (not shown in FIG. 2) located on the proximal extremity 204 of guide wire 10. The electrical contacts located in housing 212 allow for rotation of the guide wire while maintaining electrical contact with the conductive sleeves found in guide wire 10, these conductive sleeves are electrically coupled to pressure sensor 208. The electrical contacts in housing 212 are electrically connected to cable 214 that terminates in connector 32.

The connector 32 is connected to another mating connector 34 located on the interface box 24. Interface box 24 provides signal buffering and voltage level adjustments between guide wire 10 and pressure monitoring console 28. The electrically conductive sleeves 302, 304 and 306, which are located at the proximal extremity of guide wire 10, are shown in FIG. 3.

In FIG. 4 there is shown an electrical schematic representation of the pressure sensor 208 which comprises two variable resistors 402 and 404 whose resistance values vary with changes in pressure as is known in the art. Pressure sensor 208 can be a semiconductor having a diaphragm as is well known in the art. The two resistors 402 and 404 are connected to the three electrically conductive sleeves or bands 302, 304 and 306 located on the proximal extremity of guide wire 10 as shown.

FIG. 5 shows an exploded isometric view of the prior art rotary connector assembly 220 including rotartary connector 210 and housing 212. In operation, the proximal extremity of the flexible elongate member or pressure guide wire 10 is inserted into bore 501 with one hand while holding the rotary connector with the other hand. The nose piece 503 and the collar 504 are then pulled with fingers in a proximal direction against the force of the spring 508 to release the collet 502 and allow it to open. The guide wire 10 can then enter the bore 501 and pass through the inside of collet 502 and through bearing 510. The guide wire 10 is then pushed further in until conductive sleeve 302 is making electrical contact with contact member 546, conductive sleeve 304 is making electrical contact with contact member 544 and conductive sleeve 306 is making electrical contact with contact member 542.

Housing members 514 and 530 retain contacts 542, 544 and 546. A retaining ring 506, which is inserted through an opening in bearing 510, engages with and retains collet 502. Connector 32 provides an interconnection with the interface box 24 through a cable as shown in FIG. 1.

A problem with the above noted design is that sometimes as the guide wire 10 is being rotated, the contact resistance between electrically conductive sleeves 302, 304 and 306 located on the guide wire 21 and the corresponding electrical contacts located in housing 212 varies. This contact resistance variation is assumed to be caused by microscopic particles that get lodged between the pressure guide wire's conductive bands 302, 304 and 306 and the corresponding spring contacts 546, 544 and 542. This change in contact resistance causes an error in the pressure measurement as determined by pressure monitoring console 28, since this change in contact resistance affects the measurement of pressure sensor resistors 402 and 404.

An electrically equivalent circuit showing this change in contact resistance is shown in FIG. 8. Pressure sensor 208 is shown coupled to sleeve contacts (conductive bands) 302, 304 and 306 via electrical conductors. Sleeve contact 302 is shown coupled to contact 546, sleeve contact 304 is shown coupled to contact 544 and sleeve contact 306 is shown coupled to contact 542. Variable resistors 802, 804 and 806 represent the variable contact resistance caused by the rotating connector interface. The resistance of resistors 802, 804 and 806 vary as the pressure guide wire is rotated. As shown, contact resistance 802 is in series with sensor resistor 402 and contact resistance 806 is in series with sensor resistor 404 and thus any change in the contact resistance will affect the measurement of sensor 208. A need thus exists in the art for a solution that can minimize electrical interconnection problems as the one described above.

BRIEF DESCRIPTION OF THE DRAWINGS

The features of the present invention, which are believed to be novel, are set forth with particularity in the appended claims. The invention, together with further objects and advantages thereof, may best be understood by reference to the following description, taken in conjunction with the accompanying drawings, in the several figures of which like reference numerals identify like elements, and in which:

FIG. 3 shows the prior art guide wire showing the electrically conductive sleeves located at the proximal extremity of the guide wire. FIG. 4 shows an electrical representation of the prior art pressure sensor attached to the electrically conductive sleeves.

DETAILED DESCRIPTION OF THE PREFERRED EMBODIMENT

Figure 1:
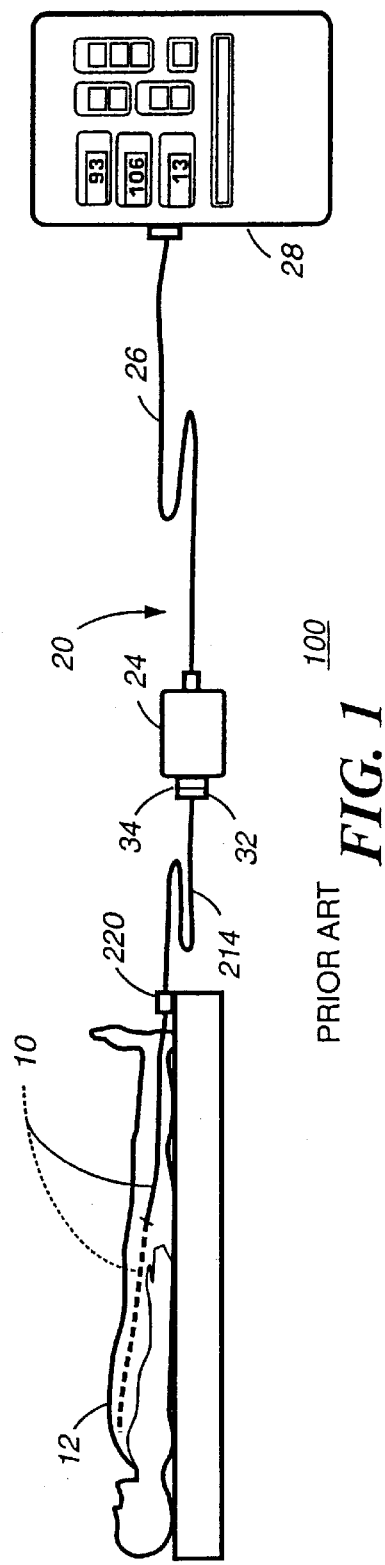
FIG. 1 is an illustration showing a prior art guide wire in conjunction with a patient undergoing a catheterization procedure for diagnosis or treatment.
Figure 2:
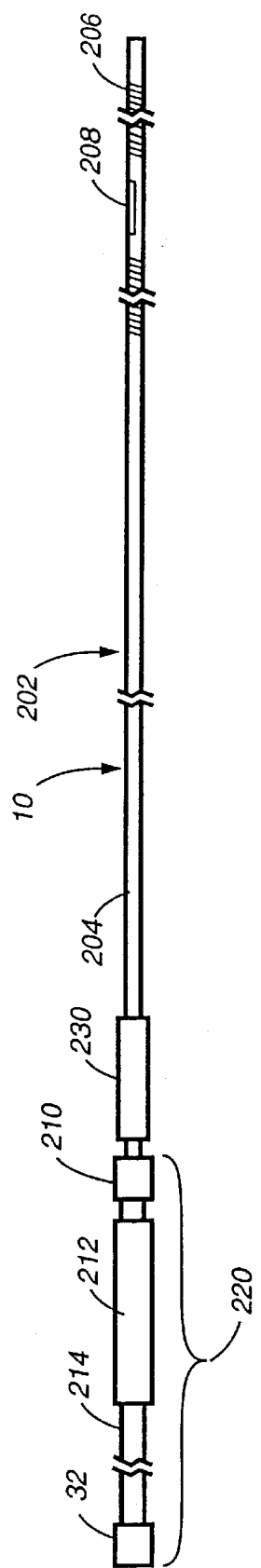
FIG. 2 shows a more detailed view of the prior art guide wire attached to a rotating connector assembly.

While the specification concludes with claims defining the features of the invention that are regarded as novel, it is believed that the invention will be better understood from a consideration of the following description in conjunction with the drawing figures, in which like reference numerals are carried forward.

Figure 5:
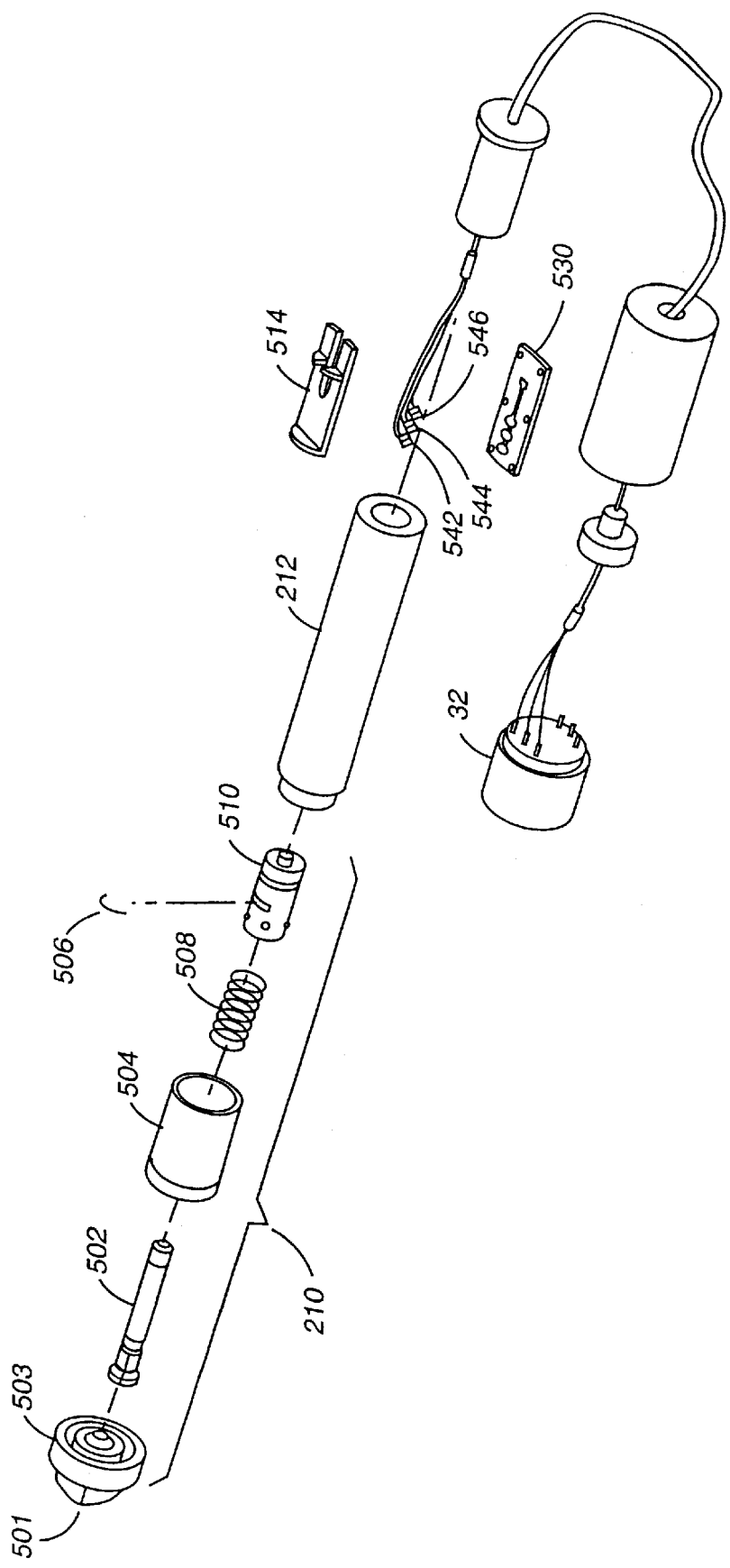
FIG. 5 shows an exploded view of the prior art rotary connector and housing used to receive the pressure guide wire.
Figure 6:
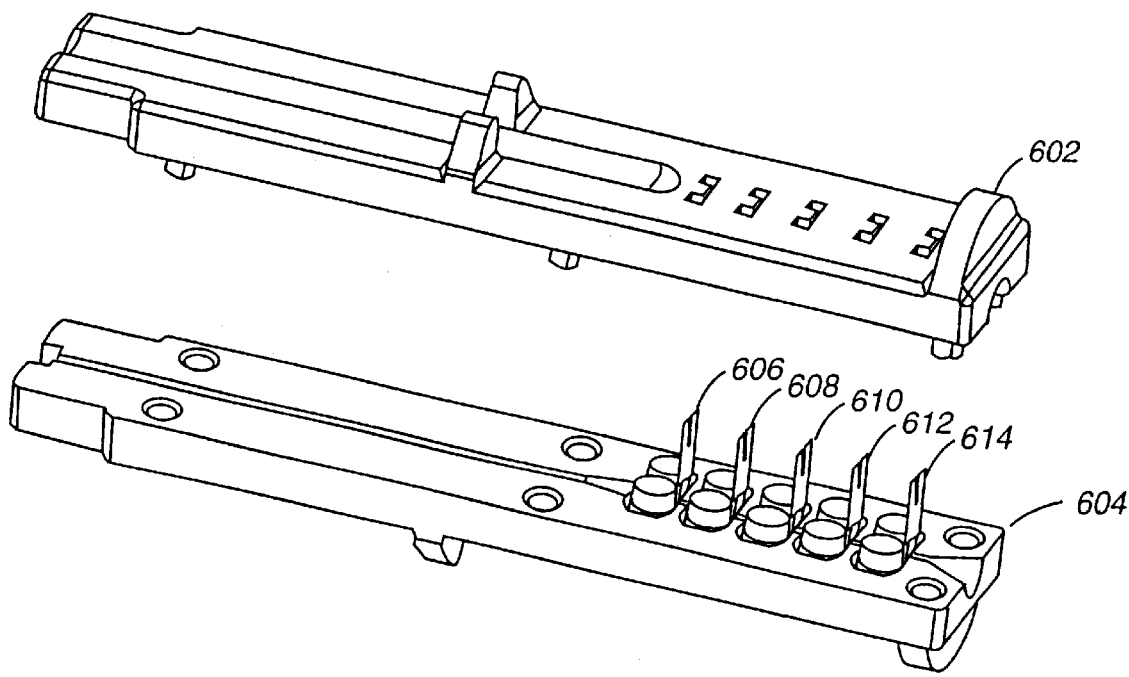
FIG. 6 shows a housing having contacts in accordance with the present invention.
Figure 7:
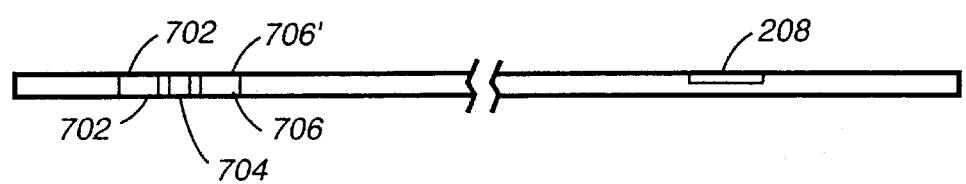
FIG. 7 shows a view of a pressure guide wire in accordance with the invention.
Figure 8:
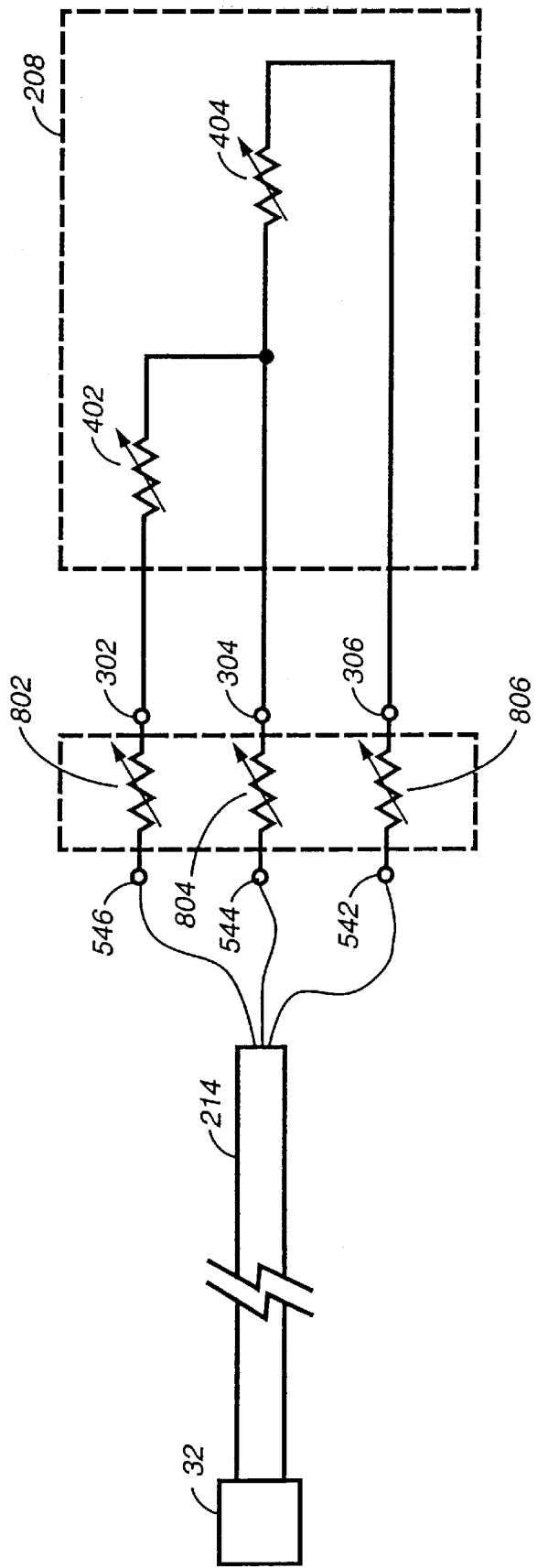
FIG. 8 shows an electrical representation of the prior art electrical interconnection between the guide wire and the rotary connector.

Referring now to FIG. 6, there is shown an electrical contact assembly 600 in accordance with the invention. Assembly 600 includes first and second housing members 602 and 604 that retain five guide wire spring contacts 606–614. Assembly 600 takes the place of housing members 514 and 530 and contacts 542, 544 and 546 in FIG. 5. In FIG. 7, there is shown a pressure guide wire 700 in accordance with the invention. Similar to guide wire 10, pressure guide wire 700 includes three conductive sleeves or contacts 702, 704 and 706. However, unlike guide wire 10, the two outer contacts 702 and 706 are wider than the middle contact 704. The wider sleeve contact 702 and 706 are designed so that they can make contact with two corresponding contacts each from among contacts 606–614. Guide wire sleeve contact 702 is designed to make an electrical connection with contacts 606 and 608 and sleeve contact 706 makes electrical connection with contacts 612 and 614 when guide wire 700 is placed in assembly 600. The center guide wire sleeve contact 704 makes electrical connection with center contact 610. Housing assembly 600 has been designed to be backward compatible and will accept either the newly designed guide wire 700 or the prior art guide wire 10. When guide wire 10 is inserted into assembly 600, sleeve contact 306 makes connection with contact 612, sleeve contact 304 makes connection with contact 610 and sleeve contact 302 makes connection with contact 608.

Figure 9:
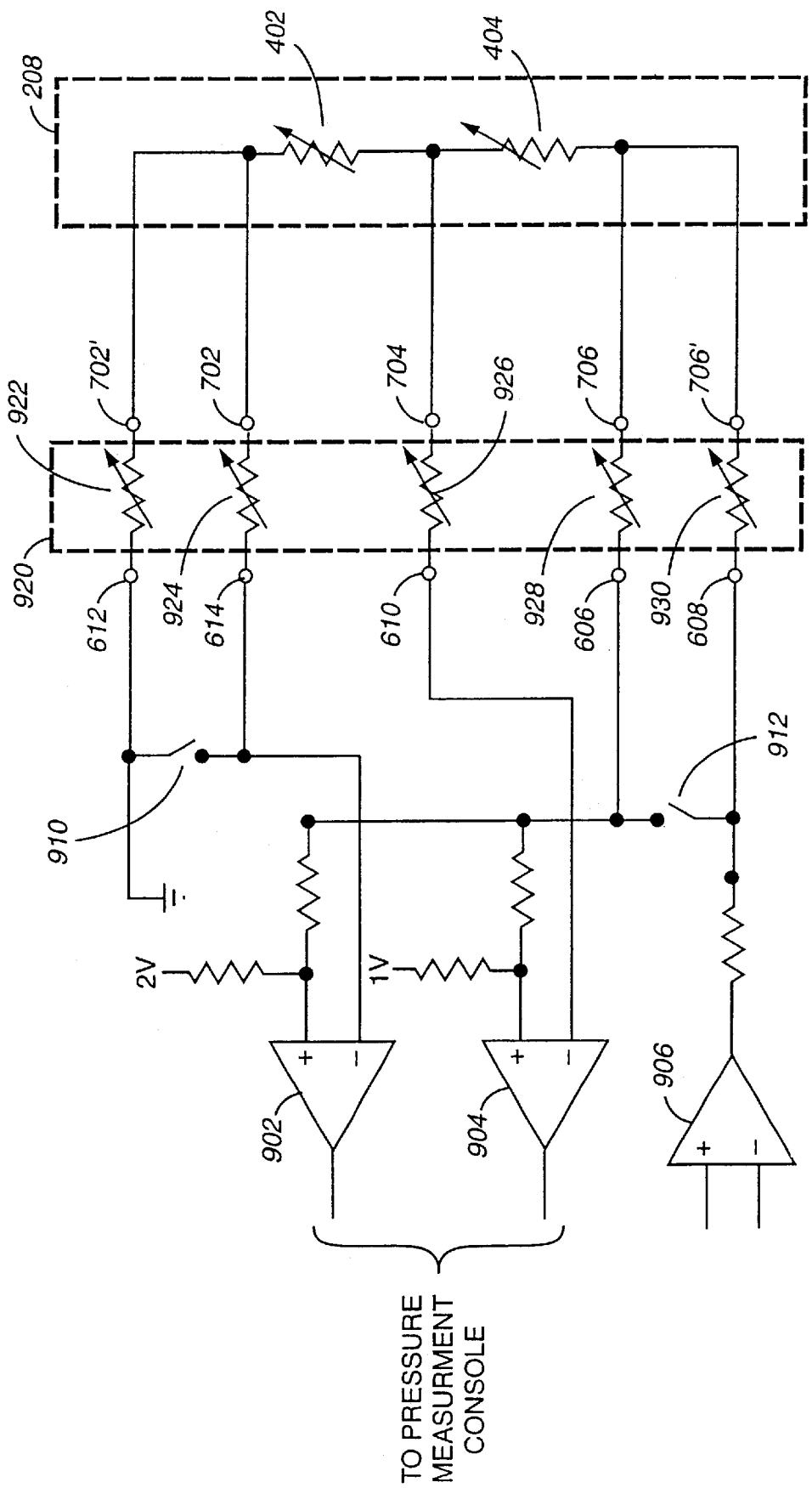
FIG. 9 shows an electrical representation of the electrical interconnection between the guide wire and rotary connector in accordance with the invention.

In FIG. 9, there is shown a simplified electrical representation of the preferred embodiment precision interconnect circuit which solves for the variable contact resistance's and provides for backward compatibility with both the old pressure guide wire 10 and the new pressure wire 700. The pressure sensor 208 is coupled to sleeve contacts 702, 702', 704, 706 and 706' when a new pressure guide wire 700 is being used. When an old pressure guide wire 10 is being used, contacts 702' and 706' are not utilized since the outer sleeve contacts are not as wide as those shown in pressure wire 700. In FIG. 9, contacts 702' and 706' are simply representing the extra wide sleeve contacts found in contacts 702 and 706 as shown in FIG. 7.

The variable contact resistance problem of the interconnection is highlighted within box 920. Sleeve contacts 702', 702, 704, 706 and 706' are coupled to corresponding contacts 614, 612, 610, 608 and 606 in the new design which form the input port for the interconnection circuit. When an old pressure guide wire 10 is attached, contacts 614 and 606 are not utilized. Switches 910 and 912 remain in the open position or first state when a new guide wire 700 is attached and are automatically placed in the closed position or second state when an old guide wire 10 is attached in response to a control signal. The control electronics for switches 910 and 912 will be discussed in detail further below. Switches 910 and 912 allow for the interconnect interface to be backward compatible and support both pressure guide wire 10 and the new pressure guide wire 700. In the interconnection interface, new pressure guide wire 700 uses a 5-wire interconnection, while the old pressure guide wire uses a 3-wire interconnection. A pair of differential operational amplifiers or precision amplifiers 902 and 904 that have high impedance inputs and are part of the interface circuit allow for three low current paths. These paths take away the effect of changes in the contact resistance (924, 926 and 928) from changes in the sensor resistors 402 and 404. A reference current is provided to the sensor resistor 402 and 404 as shown in order to generate the appropriate voltage drops used for pressure change detection.

Figure 10:
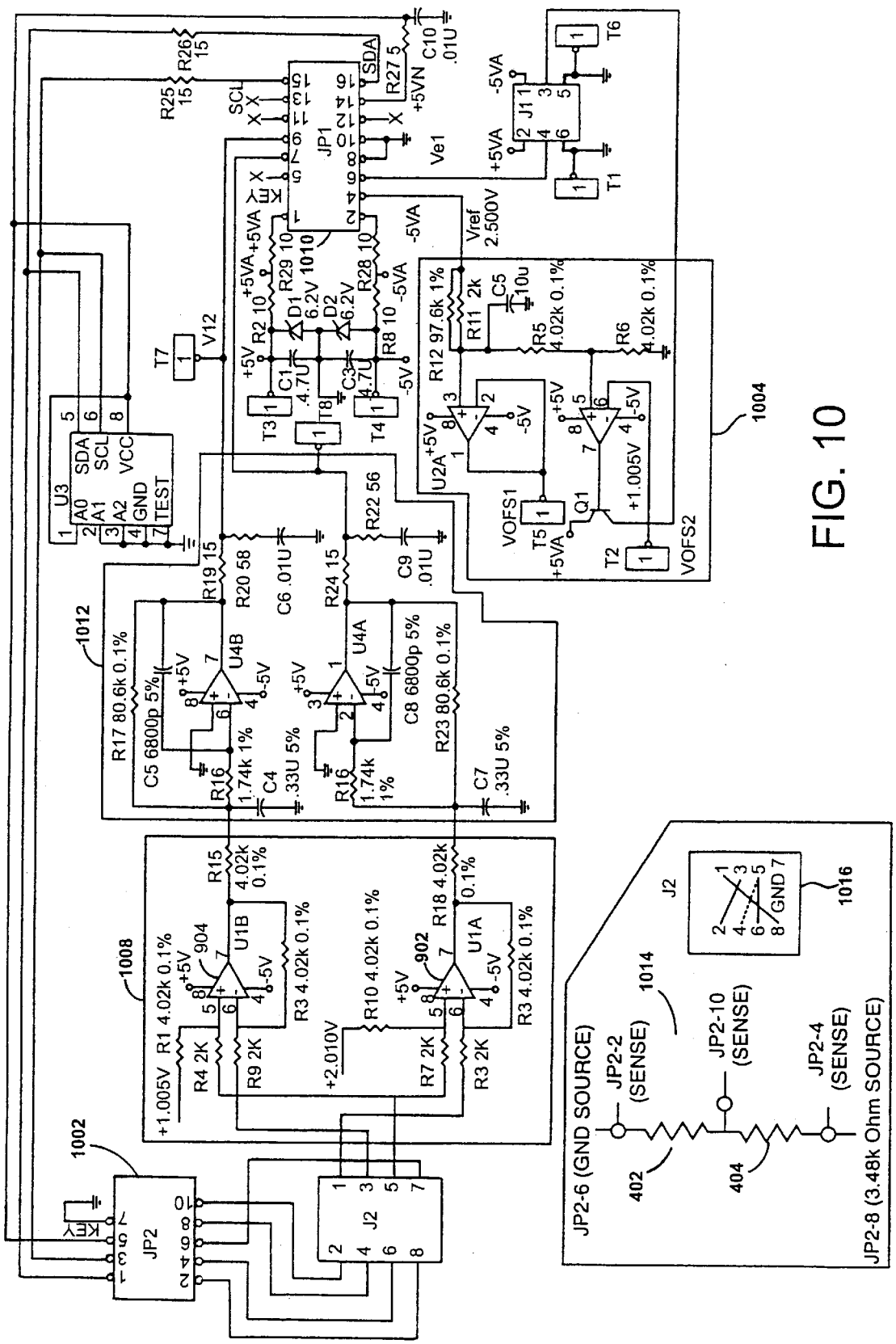
FIGS. 10 and 11 show electrical schematics for the interface circuit in accordance with the present invention.
Figure 11:
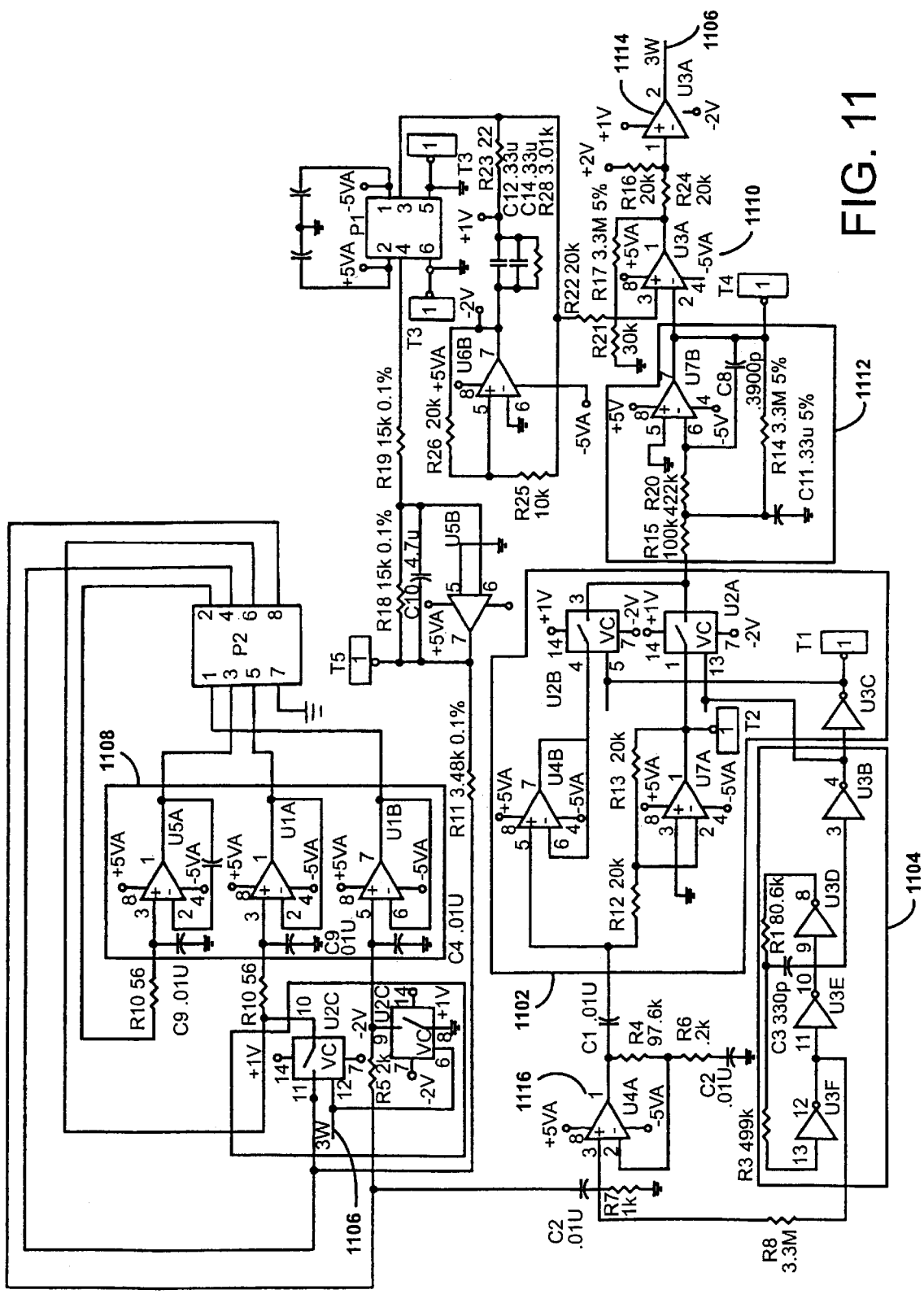

Referring now to FIGS. 10 and 11, there is shown a full electrical schematic for the interface circuit which replaces the electronics found in interface box 24. The circuitry shown in FIGS. 10 and 11 includes not only the circuitry needed to perform the precision interconnection as described above, but also provides the necessary signal conditioning circuitry needed to match the signal from the pressure sensor 208 to the pressure measurement console 28. The signal conditioning circuitry will not be discussed in detail since it is not needed in the understanding of the present invention.

The circuit shown in FIG. 10 is the mother board and the circuit shown in FIG. 11 is a daughter board which in the preferred embodiment comprise two separate printed circuit boards which are coupled together. The two circuit boards are coupled together using jack connectors J1 and J2 found in the circuit of FIG. 10 which mate with corresponding plug connectors P1 and P2 located on the circuit of FIG. 11.

Connector "JP2" 1002 in FIG. 10 is coupled to the pressure sensor resistors 402 and 404 which are coupled through via connectors 32 and 34 into the interface circuitry. The five sensor contacts are coupled to pins 2, 4, 6, 8 and 10 of connector JP2 as shown in diagram 1014. Differential amplifiers 902 and 904 as previously shown in FIG. 9 that are part of amplifier stage 1008, provide a gain of approximately two. The output of these amplifiers are fed into a 2 pole, 250 Hertz low pass filter (LPF) stage 1012 which provides for a gain of approximately twenty. The outputs of the LPF stage 1012 are coupled to connector "JP1" 1010 that in turn couples into the pressure monitoring console 28. Pins 7 and 9 of connector JP1 are inputs to the pressure monitoring console, while pins 1, 2, 4, 6, 8, 10, 14, 15 and 16 are signals coming from the pressure console 28 into the interface circuitry. Although not important to the understanding of the present invention, circuit block 1004, provides offset voltage correction for the interface between the pressure guide wire 700 and the pressure monitoring console 24. Box 1016 shows the internal interconnections of connector J2.

In FIG. 11, operational amplifiers U5A, U1A and U1B form a buffer stage 1108 that provides signal buffering. Block 1104 forms an oscillator circuit that provides a signal of about 10–12 kilohertz. This signal is used to determine whether an old pressure guide wire 10 or a new pressure guide wire 700 is coupled to the interface circuitry in accordance with the present invention. A synchronous demodulator circuit 1102 takes the oscillating signals and provides a control signal 1106 that is used to control switches 910 and 912. Switches 910 and 912 remain open when pressure sensor 700 is attached and are closed when pressure wire 10 is attached. The output of demodulator circuit 1102 passes through a two pole 30 Hertz low pass filter stage 1112 having a gain of approximately thirty.

Figure 12:
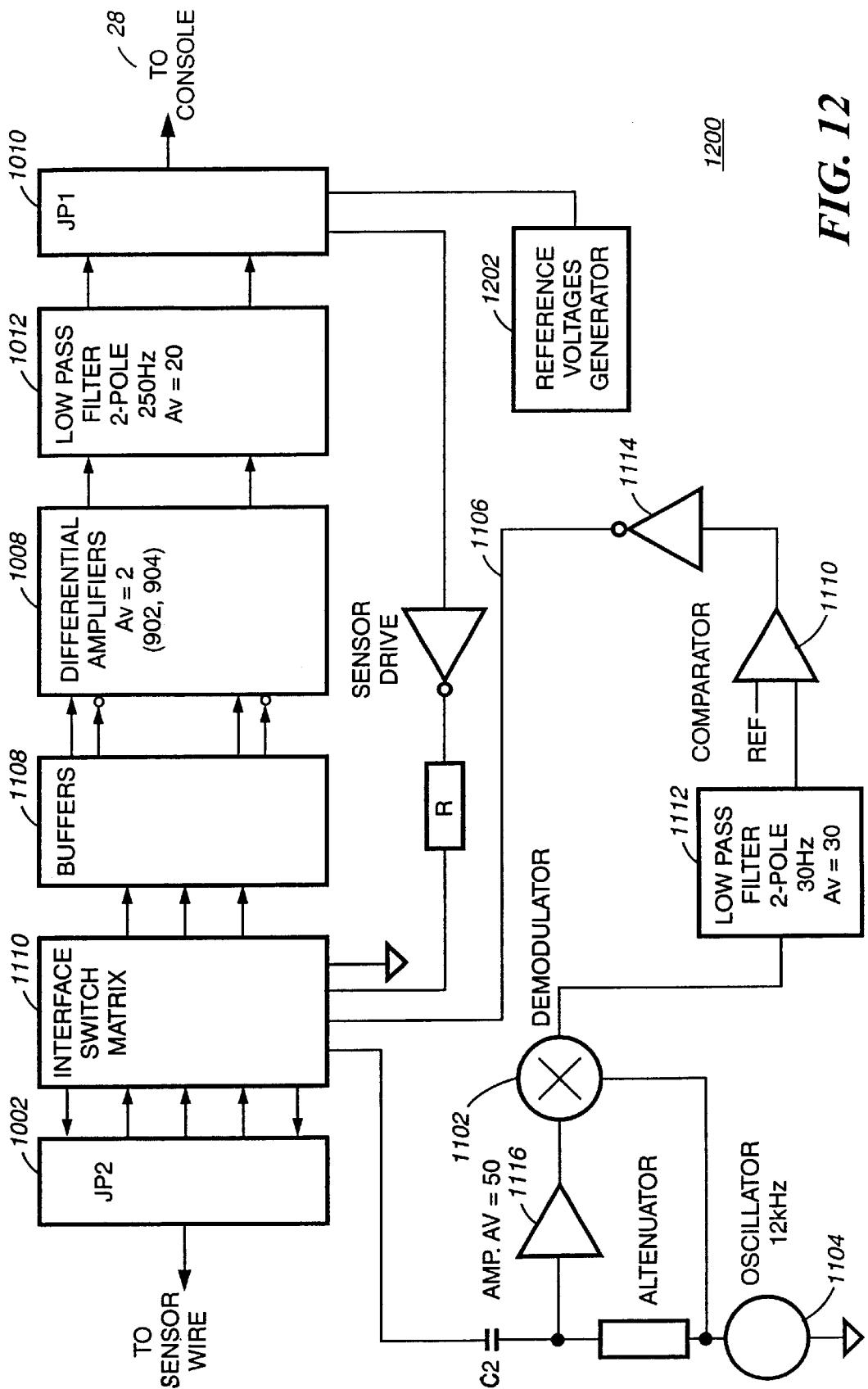
FIG. 12 shows a simplified block diagram of the electrical schematics shown in FIGS. 10 and 11 in accordance with the invention.

FIG. 12 shows a simplified block diagram of the electrical schematics of FIGS. 11 and 12 as interface circuit 1200. Pressure wire 700 is coupled to connector 1002 that is in turn coupled to the interface switch circuit 1110 comprising the two digital switches 910 and 912. The output of the digital switches is passed through a buffer stage 1108 prior to being sent to the differential amplifier stage 1008 comprising differential amplifiers 902 and 904. The output of the differential amplifier stage 1008 is sent to the 2 pole 250 Hertz low pass filter stage 1012 before the signals are sent to console 28. A reference voltage generator stage 1202 provides the necessary voltages to the circuit.

As previously mentioned in order to provide for backward compatibility between the old pressure wire 10 and the new pressure wires 700, an oscillator 1104 and demodulator 1102 are used to provide a control signal 1106 which either closes switches 910 and 912 or leaves them in the open position. When a new pressure wire 700 is detected, the control signal 1106 leaves the switches 910 and 912 in the open state, while if the old pressure wire 10 is detected control signal 1106 causes the switches to go to the closed state. By using a high frequency (10–12 Kilohertz) signal having low amplitude to make the switching determination between the 3-wire and 5-wire guide wires, prevents any stray noise and interference from affecting the control signal. Also, the use of such a low amplitude-oscillating signal prevents the signal from affecting the measurement of pressure sensor resistors 402 and 404.

A large signal at capacitor C2 causes control signal 1106 at the output of inverter 114 to be logic high closing the switches 910 and 912 indicating a 3-wire pressure wire 10 is connected to the interface circuit. While a low signal at capacitor C2 caused by the connection of a 5-wire pressure wire 700 causes the control signal 1106 to be at a low logic level leaving switches 910 and 912 in the open position.

The present invention with its use of high input impedance differential amplifiers 902 and 904 to measure pressure sensor resistors 402 and 404 avoids the problem caused by changing contact resistance 922–930. Also, the automatic switching technique disclosed above provides for a system which is backward compatible between pressure guide wires 10 and 700.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as defined by the appended claims. For example, although the preferred embodiment has discussed forming a precision interconnect for a rotating connection, the present invention is not so limited and can be used for non-rotating connections. The present invention can be used for not only with a pressure guide wire it can be used with other devices that need proper measurement of electrical parameters from the device. Also, instead of monitoring a pressure sensor 208 utilizing two resistors 402 and 404, the present invention can be used to provide a precision interconnect for devices having any number of resistors. If the number of resistors that need to be monitored change, a change has also to be made as to the number of monitoring devices such as differential op-amps 902 and 904 need to be used.

What is claimed:

1. A precision interconnect circuit, comprising:

an input port for receiving a first or second pressure guide wire;

an interface coupled to the input port, the interface operational in a first and a second state; and an interface controller that changes the interface from the first to the second state, and wherein the first state corresponds to receiving the first guide wire and the second state corresponds to receiving the second guide wire.

2. A precision interconnect circuit as defined in claim 1, wherein the first and second pressure guide wires both include a pressure sensor comprising at least one resistive element and the input port includes a high input impedance device electrically coupled to the at least one resistive element.

3. A precision interconnect circuit as defined in claim 1, wherein the interface provides an electrical interface to a pressure monitoring console for displaying pressure measurement.

4. A precision interconnect circuit as defined in claim 1, wherein the input port further comprises a plurality of spring contacts for electrically connecting the input port to conductive sleeves on the guide wire.

5. A precision interconnect circuit as defined in claim 1, wherein the interface controller comprises a control circuit for automatically switching the interface from the first state to the second state.

6. A precision interconnect circuit as defined in claim 1, wherein the interface includes a switch for switching between the first and the second state.

7. A precision interconnect circuit, comprising:

an input port for receiving a first or second pressure guide wire;

an interface switch coupled to the input port, the interface switch operational between a first and second state; and a control circuit coupled to the interface switch for providing a control signal to the interface switch for switching the interface switch from the first to the second state, wherein the control signal has a different logic level depending on which of the first or second guide wires is coupled to the input port.

8. A precision interconnect circuit as defined in claim 7, wherein the control circuit further provides a reference current to the interface switch for detecting pressure change.

9. A precision interconnect circuit, comprising:

an input port for receiving a first or second pressure guide wire;

an interface switch coupled to the input port the interface switch operational between a first and second state; and a control circuit coupled to the interface switch for providing a control signal to the interface switch for switching the interface switch from the first to the second state, wherein the control circuit comprises an oscillator and demodulator coupled to the input port.

10. A precision interconnect circuit as defined in claim 9, wherein the oscillator provides an oscillation signal which is used by the control circuit to determine which of the first or second pressure guide wire is attached to the input port.

11. A precision interconnect circuit as defined in claim 9, wherein the control circuit further comprises a low pass filter coupled to the demodulator.

12. A precision interconnect circuit as defined in claim 11, wherein the control circuit further comprises a comparator coupled to the low pass filter.

13. A precision interconnect circuit, comprising:

an input port for receiving a first or second pressure guide wire, wherein the first and second pressure guide wires both include a pressure sensor comprising at least one resistive element and the input port includes a high input impedance device electrically coupled to the at least one resistive element and wherein the high input impedance device comprises a differential operational amplifier which measures the voltage drop across the at least one resistive element;

an interface switch coupled to the input port, the interface switch operational between a first and second state; and a control circuit coupled to the interface switch for providing a control signal to the interface switch for switching the interface switch from the first to the second state.

14. A method for operating a precision interconnect circuit, comprising:

receiving a first guide wire or a second guide wire in an input port;

generating a control signal for an interface coupled to the input port; and switching the interface to one of either a first state or a second state in response to the generated control signal, wherein the first state corresponds to receiving the first guide wire and the second state corresponds to receiving the second guide wire.

15. A method as defined in claim 14, wherein the control signal is provided by a control circuit.

16. A method as defined in claim 15, wherein the control circuit comprises an oscillator and a demodulator coupled to the input port.

17. A method as defined in claim 16, wherein the oscillator provides an oscillation signal which is used by the control circuit for determining which of the first guide wire or second guide wire is attached to the input port.

18. A method as defined in claim 14, wherein the first guide wire and second guide wire both include a pressure sensor comprising at least one resistive element and the input port includes a high input impedance device electrically coupled to the at least one resistive element.

19. A method as defined in claim 18, wherein the high input impedance device comprises a differential amplifier which measures the voltage drop across the at least one resistive element.

20. A method as defined in claims 16, wherein the control circuit further comprises a low pass filter coupled to the demodulator.

21. A method as defined in claim 20, wherein the control circuit further comprises a comparator coupled to the low pass filter.

22. A method as defined in claim 15, wherein the control circuit further provides a reference current to the interface for detecting pressure change.

* * * * *